(12) United States Patent
Johnstone (10) Patent No.: US 10,945,745 B2
(45) Date of Patent: Mar. 16, 2021

(54) VARIABLE CURVE JIG FOR AN INTRAMEDULLARY DEVICE

(71) Applicant: Grampian Health Board, Aberdeen (GB)

(72) Inventor: Alan Johnstone, Aberdeen (GB)

(73) Assignee: GRAMPIAN HEALTH BOARD, Aberdeen (GB)

( * ) Notice: Subject to any disclaimer, the term of this patent is extended or adjusted under 35 U.S.C. 154(b) by 389 days.

(21) Appl. No.: 15/776,278

(22) PCT Filed: Nov. 18, 2016

(86) PCT No.: PCT/GB2016/053597
§ 371 (c)(1),
(2) Date: May 15, 2018

(87) PCT Pub. No.: WO2017/085499
PCT Pub. Date: May 26, 2017

(65) Prior Publication Data
US 2020/0253623 A1    Aug. 13, 2020

(30) Foreign Application Priority Data
Nov. 18, 2015   (GB) .................................... 1520322

(51) Int. Cl.
*A61B 17/17*    (2006.01)
*A61B 90/00*    (2016.01)
(Continued)

(52) U.S. Cl.
CPC ...... *A61B 17/1717* (2013.01); *A61B 17/1703* (2013.01); *A61B 17/1725* (2013.01); *A61B 17/72* (2013.01); *A61B 2017/00017* (2013.01); *A61B 2017/0092* (2013.01); *A61B 2090/3966* (2016.02); *A61B 2090/3983* (2016.02)

(58) Field of Classification Search
CPC . A61B 17/17; A61B 17/1703; A61B 17/1717; A61B 17/1721; A61B 17/1725
See application file for complete search history.

(56) References Cited

U.S. PATENT DOCUMENTS 4,667,664 A  *  5/1987  Taylor ................ A61B 17/1725
606/64
4,865,025 A  *  9/1989  Buzzi ................. A61B 17/1703
606/96
(Continued)

FOREIGN PATENT DOCUMENTS

EP    0 354 395    2/1990
EP    1 719 465    11/2006
(Continued)

OTHER PUBLICATIONS

International Search Report and Written Opinion issued on PCT/GB2016/053597, dated Feb. 20, 2017.

*Primary Examiner* — Eric S Gibson
(74) *Attorney, Agent, or Firm* — Foley & Lardner LLP (57) ABSTRACT

The present invention relates to an apparatus for affixing intramedullary devices in a body. In particular the apparatus comprises a jig affixable to an intramedullary nail. There is also provided a method of determining the position of holes to be drilled through a bone which align with holes in the nail.

19 Claims, 10 Drawing Sheets

(51) Int. Cl.
*A61B 17/72* (2006.01)
*A61B 17/00* (2006.01)

(56) References Cited

U.S. PATENT DOCUMENTS

| | | | |
|---|---|---|---|
| 5,281,224 A | 1/1994 | Faccioli et al. | |
| 5,766,179 A | 6/1998 | Faccioli et al. | |
| 6,039,739 A | 3/2000 | Simon | |
| 6,514,253 B1 | 2/2003 | Yao | |
| 7,481,815 B2 * | 1/2009 | Fernandez | A61B 17/1703 606/97 |
| 8,231,629 B2 * | 7/2012 | Lerner | A61B 17/1725 606/87 |
| 8,628,538 B2 * | 1/2014 | Arlettaz | A61B 17/1725 606/104 |
| 8,685,034 B2 * | 4/2014 | Giersch | A61B 17/1725 606/98 |
| 8,795,287 B2 * | 8/2014 | Fritzinger | A61B 17/1725 606/98 |
| 8,945,136 B2 * | 2/2015 | Overes | A61B 17/1725 606/98 |
| 8,968,324 B2 * | 3/2015 | Atkinson | A61B 17/1725 606/98 |
| 8,986,315 B2 * | 3/2015 | Durante | A61B 17/1725 606/96 |
| 9,107,709 B2 * | 8/2015 | Wieland | A61B 17/1725 |
| 9,820,760 B2 * | 11/2017 | Purohit | A61B 5/062 |
| 10,390,844 B2 * | 8/2019 | Wieland | A61B 17/1725 |
| 10,485,562 B2 * | 11/2019 | Luo | A61B 17/1725 |
| 10,492,803 B2 * | 12/2019 | Machamer | A61B 17/1615 |
| 10,695,109 B2 * | 6/2020 | Karg | A61B 17/1725 |
| 2003/0135211 A1 * | 7/2003 | Cho | A61B 17/1725 606/62 |
| 2003/0212405 A1 * | 11/2003 | Choi | A61B 17/1721 606/98 |
| 2006/0064106 A1 * | 3/2006 | Fernandez | A61B 17/1703 606/98 |
| 2008/0039857 A1 * | 2/2008 | Giersch | A61B 17/1703 606/96 |
| 2008/0058829 A1 * | 3/2008 | Buscher | A61B 17/1703 606/96 |
| 2008/0281331 A1 * | 11/2008 | Fritzinger | A61B 17/1725 606/96 |
| 2009/0306665 A1 * | 12/2009 | Lerner | A61B 17/1703 606/64 |
| 2010/0160913 A1 | 6/2010 | Scaglia | |
| 2010/0179550 A1 * | 7/2010 | Schreiber | A61B 17/1725 606/62 |
| 2010/0274254 A1 * | 10/2010 | Boileau | A61B 17/7098 606/93 |
| 2011/0245885 A1 * | 10/2011 | Powell | A61B 17/1725 606/86 R |
| 2012/0239039 A1 * | 9/2012 | Nardini | A61B 17/1725 606/64 |
| 2012/0253354 A1 | 10/2012 | Arlettaz et al. | |
| 2012/0303038 A1 * | 11/2012 | Durante | A61B 17/1703 606/96 |
| 2013/0110119 A1 * | 5/2013 | Atkinson | A61B 17/1725 606/98 |
| 2013/0172890 A1 * | 7/2013 | Limouze | A61B 17/8872 606/62 |
| 2014/0364859 A1 * | 12/2014 | Wieland | A61B 90/39 606/97 |
| 2015/0305791 A1 * | 10/2015 | Purohit | A61B 5/062 606/96 |
| 2018/0140310 A1 * | 5/2018 | Machamer | A61B 17/1725 |
| 2018/0280069 A1 * | 10/2018 | Barmes | A61B 17/1775 |
| 2019/0175232 A1 * | 6/2019 | Karg | A61B 17/1725 |
| 2020/0069318 A1 * | 3/2020 | Machamer | A61B 17/7233 |
| 2020/0113609 A1 * | 4/2020 | Aneja | A61B 17/744 |

FOREIGN PATENT DOCUMENTS

| | | | |
|---|---|---|---|
| EP | 1 854 611 | 11/2007 | |
| JP | 2018149273 A * | 9/2018 | ......... A61B 17/7233 |
| WO | WO-2008/017501 | 2/2008 | |
| WO | WO-2008/053264 | 5/2008 | |
| WO | WO-2012/162607 | 11/2012 | |
| WO | WO-2013/018026 | 2/2013 | |
| WO | WO-2014/048447 | 4/2014 | |
| WO | WO-2015/122807 | 8/2015 | |
| WO | WO-2015/164689 | 10/2015 | |

* cited by examiner

Long Arm

Medium Arm

Short Arm

Guide Block

Adjustment Screw

Attachment Screw

Clamping Plate

VARIABLE CURVE JIG FOR AN INTRAMEDULLARY DEVICE

CROSS REFERENCE TO RELATED APPLICATIONS

The present application is a U.S. National Stage of International Application No. PCT/GB2016/053597 filed on Nov. 18, 2016, which claims priority from GB 1520322.7, filed on Nov. 18, 2015, the entire disclosures of which are incorporated herein by reference.

The present invention relates to a variable curve jig for affixing intramedullary device, in particular an intramedullary nail in a body. There is also provided a method of determining the position of holes to be drilled through a bone which align with holes in the nail.

BACKGROUND TO THE INVENTION

It is common practice to support fractures in long bones, such as tibia and femur, by implants such as intramedullary nails. The intramedullary device is inserted into the medullary canal of the long bone, and is held in place by screws or pins that are driven laterally through the bone at each end of the nail. The screws also pass through pre-drilled holes in the end of the intramedullary nail, thereby reducing or preventing movement of the nail/bone while the fracture is healing. Holes must be bored laterally through the bone "blind" in order to insert the screws, and these must be aligned with the pre-drilled holes in the ends of the intramedullary nail. It can be very difficult to accurately predict where the holes at the distal end of the intramedullary device are located. In order to position and drill the holes accurately in the bone a jig is commonly employed to correctly locate the holes in the nail closest to the jig attachment.

The jig is attached to the protruding (proximal) end of the nail after insertion of the nail into the medullary canal, and typically extends generally parallel to the nail. The jig has pre-drilled holes that align with the holes in nail when the jig and the nail are properly attached and aligned. This works quite satisfactorily for the proximal holes to be drilled through the bone, but since the jig is only attached to the nail at one end, and the jig and nail can be quite long (up to around 50 cm), it can be very difficult to align the distal holes in the jig with the distal holes in the nail, and this is the reason why jigs tend to be short and only identify the positioning of the proximal holes.

In particular, intramedullary devices tend to bend along their longitudinal profile, and this bend tends to be exaggerated upon implantation into a long bone. Significantly, the bend of the intramedullary device cannot be predicted, as each bone bends slightly differently. The bend of the intramedullary device following implantation makes predicting the location of the holes at the distal end of the intramedullary device even more challenging.

STATEMENT OF INVENTION

According to a first aspect of the present invention, there is provided an apparatus for affixing an intramedullary device having a curved longitudinal profile, the apparatus comprising:

a jig affixable to the intramedullary device at a proximal end, the jig comprising a guide arm having a distal end movable relative to the intramedullary device, said distal end movable between a non-aligned position in which the distal end is laterally spaced from the distal end of the intramedullary device, and an aligned position in which the distal end is aligned with the distal end of the intramedullary device, a second arm biased away from the guide arm in the aligned position;

drill guiding means suitable for guiding affixment means towards the distal end of the intramedullary device, alignment adjustment mechanism to adjust the alignment of the guide arm relative to the longitudinal profile of the intramedullary device, wherein in the non-aligned position, the longitudinal profile of the guide arm is curved between the proximal end and the distal end, wherein the curve of the longitudinal profile of the guide arm varies between the non-aligned position and the aligned position.

According to one embodiment, the radius of curvature of the curved longitudinal profile of the guide arm is smaller than the radius of curvature of the curved longitudinal profile of the intramedullary device, and the radius of curvature of the longitudinal profile of the guide arm is greater in the aligned position than in the non-aligned position.

According to a further embodiment, the radius of curvature of the curved longitudinal profile of the guide arm is greater than the radius of curvature of the curved longitudinal profile of the intramedullary device, and the radius of curvature of the longitudinal profile of the guide arm is smaller in the aligned position than in the non-aligned position.

Generally, the guide arm comprises a radio translucent portion and at least one radio opaque marking, suitably at or towards its distal end.

The alignment of the distal end of the guide arm and the distal end of the intramedullary device can be checked, typically with the use of an X-ray generator, generally through fluoroscopy.

The intramedullary device may be configured for use with a bone having a length of 10 cm or more, suitably 20 cm or more, more suitably 30 cm or more.

According to a further embodiment, there is provided a system including the apparatus as disclosed herein for affixing an intramedullary device, and generally an analytical instrument used to monitor the alignment of the longitudinal profile of the guide arm relative to the longitudinal profile of the intramedullary device. The system also can include a suitably programmed computer for carrying out one or more steps of fixing the intramedullary device to the patient's bone. For example, the suitably programmed computer can carry out or assist in one or more of measuring the alignment of the longitudinal profile of the guide arm relative to the longitudinal profile of the intramedullary device; and displaying information relating to the alignment of the guide arm and the intramedullary device. The system can also include an adjustment mechanism to assist in altering the alignment of the guide arm relative to the intramedullary device.

According to a further embodiment there is provided a kit of parts comprising an apparatus for affixing an intramedullary device as described herein and instructions for use.

Definitions

The distal end of the intramedullary device is used to refer to the end of the intramedullary device which in use is positioned within the bone away from the opening in the body/bone (the protruding end of the intramedullary device).

Likewise, the distal end of the guide arm is used to refer to the end of the guide arm which is positioned away from the opening in the bone/body, generally away from the position where the jig is attached to the intramedullary device.

The proximal end of the intramedullary device and guide arm is used to refer to the end thereof positioned towards the opening in the bone/body in use.

At or towards the distal portion generally indicates less than 20% of the length of the relevant body nearest to the distal end, typically 5 to 20%, suitably 10% or less, more suitably 2 to 10% of the length of the relevant body nearest to the distal end.

Throughout the Application, where apparatus is described as having, including, or comprising specific components, or where processes or methods are described as having, including, or comprising specific process steps, it is contemplated that apparatus of the present teachings also consist essentially of, or consist of, the recited components, and that the methods of the present teachings also consist essentially of, or consist of, the recited process steps.

In the Application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of an apparatus, or a method described herein can be combined in a variety of ways, whether explicit or implicit herein.

The use of the terms "include," "includes", "including," "have," "has," or "having" should be generally understood as open-ended and non-limiting unless specifically stated otherwise. The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a +10% variation from the nominal value unless otherwise indicated or inferred.

It should be understood that the order of steps or order for performing certain actions is immaterial so long as the present teachings remain operable. Moreover, two or more steps or actions may be conducted simultaneously.

Features, aspects, integers, characteristics, or groups described in conjunction with a particular aspect, embodiment or example of the invention are to be understood to be applicable to any other aspect, embodiment or example described herein unless incompatible therewith.

DETAILED DESCRIPTION

According to a first aspect of the present invention, there is provided an apparatus for affixing an intramedullary device having a curved longitudinal profile, and at least one hole at or towards the distal end of the intramedullary device, the apparatus comprising:

a jig affixable to the intramedullary device at a proximal end, the jig comprising a guide arm having a distal end movable relative to the intramedullary device, said distal end movable between a non-aligned position in which the distal end is laterally spaced from the distal end of the intramedullary device, and an aligned position in which the distal end is aligned with the distal end of the intramedullary device, and a second arm biased away from the guide arm in the aligned position;

drill guiding means suitable for guiding affixment means towards the distal end of the intramedullary device, alignment adjustment mechanism to adjust the alignment of the guide arm relative to the longitudinal profile of the intramedullary device, wherein in the non-aligned position, the longitudinal profile of the guide arm is curved between the proximal end and the distal end, wherein the curve of the longitudinal profile of the guide arm varies between the non-aligned position and the aligned position.

Suitably, the radius of curvature of the curved longitudinal profile of the guide arm is smaller than the radius of curvature of the curved longitudinal profile of the intramedullary device, and the radius of curvature of the longitudinal profile of the guide arm is greater in the aligned position than in the non-aligned position.

Generally, in the non-aligned position, the radius of curvature of the longitudinal profile of the guide arm is at least 10% less than the radius of curvature of the curved longitudinal profile of the intramedullary device, typically at least 20%, suitably at least 30%, more suitably at least 40%.

For such embodiments, when in the non-aligned position, the guide arm of the apparatus of the present invention has an associated curvature greater than that of the intramedullary device. The guide arm provides an exaggerated bend compared to the curved longitudinal profile of the intramedullary device. This means that the adjusting mechanism would always have to be adjusted in the same direction to move the guide arm from the non-aligned to the aligned position. Accordingly, in use the surgeon would always know in which direction he will be adjusting the adjusting mechanism (generally through turning an adjustment screw) to bring about alignment of the guide arm with the intramedullary device. In addition, the curve of the intramedullary device would always be accounted for by the guide arm. The guide arm would not provide an incorrect indication of the position of the hole(s) at or towards the distal end of the intramedullary device due to the guide arm being too straight.

Alternatively, the radius of curvature of the curved longitudinal profile of the guide arm is greater than the radius of curvature of the curved longitudinal profile of the intramedullary device, and the radius of curvature of the longitudinal profile of the guide arm is smaller in the aligned position than in the non-aligned position. In such embodiments, the user would be aware that the guide arm was less curved than the IM device and would be aware that the guide arm required adjustment to increase its curve in order to bring it into alignment with the IM device.

For such embodiments, in the non-aligned position, the radius of curvature of the longitudinal profile of the guide arm is at least 10% greater than the radius of curvature of the longitudinal profile of the intramedullary device, typically at least 20% greater.

In the aligned position, the longitudinal profile of the guide arm curves from the proximal end to the distal end and remains slightly curved. This is similar in practice to the slightly curved longitudinal profile of most bones, and thus most intramedullary devices. Accordingly, the slightly curved guide arm of the apparatus of the present invention provides a more accurate indication of where the holes are likely to be located at or towards the distal end of the intramedullary device, where the holes are used to house screws or other means to fix the intramedullary device to the surrounding bone at or towards the distal end of the intramedullary device. The slight bend in the guide arm in the aligned position compensates for a deflection in the intramedullary device when the intramedullary device is implanted into a bone. The average curve of a bone such as a femoral bone is greater than the average curve of currently available intramedullary devices such as IM nails, meaning the such IM deflect upon insertion into the bone. This deflection is difficult to predict and is dependent on the curve of the bone, the material from which the intramedullary device is made and the thickness of the walls of the intramedullary device. An accurate indication of the positioning of the holes is particularly important if an indication of more than one hole in the intramedullary device is required. Where a guide arm is straight, it may be able to accurately predict the location of a single hole in the intramedullary device, but not more than one hole.

Intramedullary devices such as intramedullary (IM) nails tend to curve, generally having a radius of curvature of 150 to 300 cm, generally 190 to 300 cm. In most cases, when implanted into a bone, this curve tends to be exaggerated although can be reduced dependent upon the internal geometry of the bone. For instance, the average femoral anterior radius of curvature in a human is 120 to 136 cm (+/−36 cm), typically 114 to 120 cm. It is difficult to predict the curve of a bone as this depends on both the type of bone and the individual patient. It has been found that the femurs of black individuals tend to be straighter then the femurs of white individuals. In addition, the curve of intramedullary devices such as intramedullary (IM) nails is determined by the modulus of elasticity of the intramedullary device. Titanium IM nails tend to have a modulus of elasticity of 15 to $20 \times 10^8$ psi whereas cobalt IM nails generally have a modulus of elasticity of 35 to $40 \times 10^8$ psi. Moreover, wall thickness of the intramedullary device is an important determinant of stiffness.

Where the guide arm of a jig for affixing an intramedullary device is straight, the guide arm may accurately indicate the positioning of a single hole in the intramedullary device at or towards the distal end. A hole may be drilled through the bone to allow suitable affixment, generally a screw to be positioned through the hole in the intramedullary device to fix the intramedullary device into position. However, due to the curve of the longitudinal profile of the intramedullary device, a straight guide arm will not accurately indicate the positioning of a second or subsequent hole spaced from the proximal end of the intramedullary device. This can lead to holes being drilled through the bone in incorrect positions, with obvious adverse effects. This is significant as intramedullary devices such as IM nails are generally secured at more than one position spaced away from the proximal end of the intramedullary device.

Typically, the intramedullary device comprises at least two holes for fixing to the surrounding bone at or towards the distal end of the intramedullary device. At least one hole is generally within the 10% of the length of the intramedullary device towards the distal end, a second hole may be within 20 to 30% of the length of the intramedullary device towards the distal end. The holes are generally spaced at least 20 mm away from each other.

Typical intramedullary devices with which the apparatus of the present invention may be used include nails for implantation into bone, for instance femoral intramedullary (IM) nails, tibial IM nails, humeral IM nails, supracondylar IM nails, reconstruction IM nails, plates, or other structural support devices to be inserted into a body such as drill bits, guide wires for drills, screws such as bone screws, k-wires, blade plates and pins such as external fixator pins etc.

Where the radius of curvature of the curved longitudinal profile of the guide arm is smaller than the radius of curvature of the curved longitudinal profile of the intramedullary device, the longitudinal profile of the guide arm generally curves away from the aligned position. Typically, the longitudinal profile of the guide arm curves from the proximal end to the distal end away from the aligned position.

According to one embodiment, the curvature of the longitudinal profile of the guide arm is lessened upon movement towards the aligned position. Accordingly, upon movement to the aligned position, the guide arm is generally straightened out. In such embodiments, the guide arm is generally moved towards the second arm upon movement from the non-aligned position towards the aligned position.

Alternatively, the curvature of the longitudinal profile of the guide arm may be increased upon movement towards the aligned position. In such embodiments, the guide arm is generally moved away from the second arm upon movement from the non-aligned position towards the aligned position.

In the aligned position, the curvature of the guide arm is generally the same or very similar to the curvature of the intramedullary device, in particular once the intramedullary device has been implanted into a human bone. In the aligned position, the longitudinal profile of the guide arm suitably has a radius of curvature of 120 to 136 cm (+/−36 cm), generally 110 to 150 cm, typically 115 to 130 cm, more typically 115 to 120 cm.

According to one embodiment, the guide arm has a radius of curvature of between 125 and 135 cm, and at least three positions of alteration of curvature along its length.

The radius of curvature of the guide arm in the non-aligned position generally alters by at least degrees compared to the radius of curvature of the guide arm in the aligned position.

According to one embodiment in the non-aligned position, the longitudinal profile of the guide arm suitably has a radius of curvature of 80 cm or less, generally 40 to 70 cm, typically 50 to 70 cm, more typically 60 to 70 cm.

Alternatively, in the non-aligned position, the longitudinal profile of the guide arm may have a radius of curvature of 130 cm or more, generally 130 to 150 cm.

According to one embodiment, in the non-aligned position the gradient of the longitudinal profile of the guide arm for the 30% of the length of the intramedullary device towards the distal end is offset by from 8 to 20 degrees. Generally, the longer the guide arm, the greater the offset.

The guide arm may have a length of 30 to 35 cm and in the non-aligned position the gradient of the longitudinal profile of the guide arm for the 30% of the length of the intramedullary device towards the distal end may be offset by 7 to 11 degrees.

The guide arm may have a length of 35 to 40 cm and in the non-aligned position the gradient of the longitudinal profile of the guide arm for the 30% of the length of the intramedullary device towards the distal end may be offset by 10 to 15 degrees.

The guide arm may have a length of 40 to 45 cm and in the non-aligned position the gradient of the longitudinal profile of the guide arm for the 30% of the length of the intramedullary device towards the distal end may be offset by 13 to 17 degrees.

In the aligned position, the longitudinal profile of the guide arm is substantially coincident with the longitudinal profile of the intramedullary device in the bone.

The user of the apparatus will be aware of the direction of movement necessary to bring the guide arm into alignment, as the guide arm will be significantly out of alignment in the non-aligned position (generally by 5 degrees or more, typically 10 degrees or more).

Suitably, movement of the guide arm between the non-aligned and the aligned position occurs in a substantially lateral plane relative to the intramedullary device.

Generally, the guide arm pivots from the non-aligned position to "sweep" towards the aligned position.

The apparatus generally includes a radio transparent portion towards the distal end, and at least one radio opaque marking at or towards the distal end of the guide arm, generally within 10% of the distal end. The radio opaque markings may be provided on or in the guide arm, or may be provided adjacent to the guide arm at or towards the distal end. Generally during fixing of the intramedullary device onto the bone, the bone and intramedullary device are viewed through an X-ray generator, suitably an X-ray image intensifier. The radio opaque markings on the guide arm are superimposed onto an X-ray image of the bone containing the intramedullary device. The alignment between the distal end of the guide arm and the intramedullary device can then be checked, and slight alterations can be made to ensure that the distal end of the guide arm and the intramedullary device are substantially coincident.

The radio opaque markers may be in any suitable form. Particular mention may be made of markers in the form of lines, strips, circles and balls.

Where the radio opaque markers comprise lines, the guide arm may be adjusted into the angle of the lines are coincident with the longitudinal profile of the intramedullary device.

Typically, the radius of curvature of the intramedullary device alters at one or more positions along its longitudinal axis, resulting in the steepness of the curve altering along the length of the intramedullary device. Generally, the radius of curvature of the guide arm of the apparatus of the present invention also alters along its length. Typically, the radius of curvature of the guide arm alters along its length in both the aligned and in the non-aligned positions.

Preferably, in the non-aligned position, the radius of curvature of the longitudinal profile of the guide arm is less than the radius of curvature of the longitudinal profile of the intramedullary device at each alteration. In the non-aligned position, along its length, the guide arm is more curved than the intramedullary device along its length.

According to one embodiment, the curve of the longitudinal profile of the guide arm between the proximal and distal ends of the guide arm exaggerates every curve of the intramedullary device and the bending moment for the intramedullary device. Therefore, throughout the alignment process, the guide arm of the jig is essentially being corrected continuously throughout the length of the guide arm, at multiple points of correction.

Alternatively, in the non-aligned position, the radius of curvature of the longitudinal profile of the guide arm is greater than the radius of curvature of the longitudinal profile of the intramedullary device at each alteration. In the non-aligned position, along its length, the guide arm is less curved than the intramedullary device along its length.

According to one embodiment, the radius of curvature of the guide arm alters at approximately the same positions along its length as the positions along the intramedullary device where the radius of curvature alters. At the, or each of these positions, the radius of curvature of the curve of the longitudinal profile of the guide arm is generally less than the radius of curvature of the curve of the longitudinal profile of the intramedullary device. However, in some embodiments, at the, or each of these positions, the radius of curvature of the curve of the longitudinal profile of the guide arm may be more than the radius of curvature of the curve of the longitudinal profile of the intramedullary device.

The curve of the longitudinal profile of the guide arm is generally exaggerated at each position where the radii of curvature changes compared to the curve of intramedullary device, and there are generally numerous such positions. Accordingly, the curvature of the guide arm is corrected at numerous positions along its longitudinal axis.

Generally, the radius of curvature of the longitudinal profile of the guide arm alters at least twice along its length, generally three of four times.

Typically, the radius of curvature alters within the 50% of the length of the guide arm towards the proximal end, generally at least once within the 50% of the length of the guide arm towards the proximal end. Suitably the radius of curvature alters within the 30% of the length of the guide arm towards the proximal end, typically within the 25% of the length of the guide arm towards the proximal end.

According to one embodiment, the guide arm includes an alteration point within the 10 cm extending from the distal end According to one embodiment the radius of curvature alters within 60 to 90% of the length of the guide arm towards the proximal end, generally within the 60 to 75% of the length.

In one embodiment, the radius of curvature alters within the 30% of the length of the guide arm towards the proximal end, and within the 30% of the length of the guide arm towards the distal end.

The gradient of the curve of the guide arm typically alters by at least 2 degrees at each alteration position. Generally, at each alteration along its length, the radius of curvature of the guide arm alters by at least 3 degrees, suitably by 5 to 10 degrees.

Typically, there are 5 or less alteration positions along the length of the guide arm, generally 2 to 4 alteration positions, suitably 3 alteration positions.

In the non-aligned position, the guide arm is generally angled from the aligned position by at least 5 degrees, more generally at least 10 degrees in the non-aligned position. In the non-aligned position, the straight-line axis from the proximal to the distal end of the jig is generally disposed at an angle of at least 10 degrees from the straight-line axis from the proximal to the distal end of the intramedullary device.

In the aligned position, the initial gradient of the curve of the longitudinal profile of the guide arm is generally offset by 7 degrees or less, typically 3 to 5 degrees.

In the non-aligned position, the initial gradient of the curve of the longitudinal profile of the guide arm is generally offset by 10 degrees or more. According to one embodiment, the gradient of the curve of the longitudinal profile of the guide arm towards the distal end is offset by 10 to 15 degrees.

Alternatively, in the non-aligned position, the initial gradient of the curve of the longitudinal guide arm may be offset by 1 to 2 degrees.

According to one embodiment, the guide arm may be replaceable, and the length of the guide arm may be altered depending on the intramedullary device of interest. In general, the length of the guide arm is similar to the length of the intramedullary device, typically within 20% of the length of the intramedullary device, suitably within 10%, more suitably within 5% of the length of the intramedullary device to which the apparatus will be fixed in use.

According to one embodiment, the guide arm may have an associated length of 30 to 40 cm, generally 32 to 36 cm.

Alternatively, the guide arm may have an associated length of 35 to 45 cm, generally 38 to 42 cm.

Alternatively, the guide arm may have an associated length of 40 to 50 cm, generally 44 to 48 cm.

The apparatus of the present invention comprises a second arm, and the second arm biased away from the guide arm in the aligned position, and the guide arm is biased towards the non-aligned position. Accordingly, movement of the guide arm towards the aligned position is only achievable by overcoming the repulsive/resistive force which biases the two arms towards/away from each other.

Movement towards the aligned position is only made once the forces biasing the guide arm into the non-aligned position have been overcome. Upon movement of the guide arm towards the aligned position, the guide arm and the second arm generally stiffen. The stiffening, or tensioning of the apparatus generally occurs in all direction, but in particular in the plane of the guide arm adjustment. The tensioning of the apparatus increases the stability of the apparatus. The mechanical properties of the jig may be altered through this stiffening or tensioning. In addition, the tensioning of the apparatus makes it difficult to forcibly mal-align the jig after the aiming stage is complete.

The apparatus of the present invention has good torsional stability and provides internal biasing, rather than the guide arm being biased against the limb of the patient, and thus the apparatus is less likely to slip out of its aligned position.

Movement of the guide arm from the non-aligned towards the aligned positions may force the two arms closer together. In particular, it may be necessary to force the guide arm towards the second arm to move it towards the aligned position. In such an embodiment, the guide arm is generally more curved than the IM device in the non-aligned position.

Typically, in the initial non-aligned position, the two arms are maximally spaced from each other. Generally, the two arms are laterally spaced by 3 to 8 cm from the non-aligned position.

However, in some embodiments, movement of the guide arm from the non-aligned towards the aligned positions may force the two arms apart. In particular, it may be necessary to force the guide arm away from the second arm to move it towards the aligned position. In such an embodiment, the guide arm is generally less curved than the IM device in the non-aligned position. In such embodiments, in the non-aligned position, the two arms may be minimally spaced from each other.

According to one embodiment, the second arm and the guide arm are substantially parallel in the non-aligned position.

The second arm is generally substantially more rigid than the guide arm, generally at least twice as rigid. Typically, the second arm has a significantly greater flexural modulus than the guide arm. The second arm may be formed from a more rigid material, or it may have a greater thickness or diameter.

According to one embodiment, the thickness or diameter of the second arm is at least 3 times greater than the thickness of the guide arm.

Generally, the second arm and the guide arm are formed from the same material for ease of manufacture, and ease of cleaning.

Alternatively, the second arm and the guide arm may be formed from different materials, and the second arm may be detachable from the guide arm.

Typically, the guide arm and the second arm have square, rectangular, oval or circular cross section, generally a square or rectangular cross section.

The apparatus of the present invention generally includes an alignment adjustment mechanism.

The alignment adjustment mechanism may comprise a torque adjustor.

Generally, the alignment adjustment mechanism is fixedly attached to the guide arm. According to one embodiment, the only part of the apparatus to which the alignment adjustment mechanism is fixedly attached is the guide arm.

Generally, the alignment adjustment mechanism is mounted around or through the second arm. Suitably the alignment adjustment mechanism is not fixedly attached to the second arm. In such embodiments, the guide block may increase the stability of the apparatus by providing rotational stability, and through interacting with the geometry of the second arm.

The alignment adjustment mechanism may include a guide block, and adjustment means, for instance a member movable between an extended and non-extended position, wherein in the extended position, the guide arm is suitably in the aligned position, and in the non-extended position, the guide arm is suitably in the non-aligned position.

The member may be in the form of, or include a screw threaded device, shaft or piston which can adjust the alignment of the guide arm in small increments. The device, shaft or piston generally extends onto the upper surface of the second arm, in particular, where the guide arm is biased away from the second arm. In embodiments where the second arm has a greater associated rigidity than the guide arm, the extension of the device, shaft or piston onto the upper surface of the second arm causes the guide arm to be pulled up towards the second arm.

Typically, the screw or piston extends onto the upper surface of the second arm, and remains on the upper surface, not extending into the second arm.

Where the guide arm is biased towards the second arm, shaft or piston of the alignment adjustment mechanism generally extends onto the lower surface of the second arm. In embodiments where the second arm has a greater associated rigidity than the guide arm, the extension of the device, shaft or piston onto the lower surface of the second arm causes the guide arm to be pulled away from the second arm.

The guide block generally includes a housing suitable to accommodate the second arm.

The alignment adjustment mechanism, in particular, the guide block does not generally tilt when moving the guide arm from the non-aligned towards the aligned position. Where the guide block is mounted around the second arm, the alignment adjustment mechanism may, according to some embodiments, be movable relative to the second arm, in particular the alignment adjustment mechanism may be movable along the surface of the second arm which it contacts. This allows the positioning of the guide arm in the aligned position to mimic the positioning of the intramedullary device in the bone. The possibility of some degree of longitudinal movement along the second arm allows the guide arm some freedom.

The alignment adjustment mechanism causes the guide arm to move between a non-aligned and an aligned position. According to one embodiment, the alignment adjustment mechanism may exert a force on the guide arm direct, or alternatively on the second arm in order to cause the guide arm to move towards an aligned position. Exerting a force on the second arm can cause the guide arm to move towards the aligned position where the second arm is more rigid than the guide arm.

According to one embodiment, the alignment adjustment mechanism (in particular the guide block) includes at least one radio opaque marking.

The alignment adjustment mechanism may also include holes there through to accommodate the pin, nail or screw which is used to fix the intramedullary device into place.

A force must be applied to move the guide arm from the non-aligned to the aligned position. This is generally applied by the alignment adjustment mechanism.

The alignment adjustment mechanism is generally attached to or housed around the distal end of the guide arm. The alignment adjustment mechanism may include one or more radio opaque markings.

According to one embodiment, the jig is affixable to the intramedullary device through detachable affixment means, providing rigid engagement between the jig and the intramedullary device. The skilled man will be aware of many devices suitable for use as the detachable affixment means, for example a screw threaded device and a clamp. The detachable affixment means are detachable from both the intramedullary device and the apparatus of the present invention, promoting ease of cleaning. The apparatus of the present invention does not generally contact the intramedullary device, risking any risk of cross-contamination between patients.

In use the apparatus of the present invention does not generally contact the patient to be treated, or the intramedullary device—contact being limited to the affixment means.

According to one embodiment, the alignment of the distal end of the guide arm and the distal end of the intramedullary device may be checked with the use of an X-ray generator, and/or through the use of fluoroscopy.

The bone and intramedullary device may be viewed through the use of the X-ray generator (typically an X-ray image intensifier). Where the distal end of the guide arm includes at least one radio opaque marking, the alignment between the distal end of the guide arm and the distal end of the intramedullary device can be checked, and minor alterations in the positioning of the distal end of the guide arm can be made to ensure that the guide arm is in the aligned position.

The intramedullary device is preferably fixed in at least two places, generally at least two places at or towards the distal end of the intramedullary device.

The intramedullary device is generally fixed to the surrounding bone by a hole being made in the bone, and a pin or screw being positioned from the bone through a hole in the intramedullary device.

According to one embodiment, a guide wire may be inserted through the hole in the bone prior to positioning of the pin or screw.

The intramedullary device is generally implanted in the medullary canal of a bone.

According to one embodiment, the apparatus is affixable to the intramedullary device through detachable affixment means and the apparatus does not contact the patient or the intramedullary device during fixing thereof.

The apparatus of the present invention maybe suitable to support a fracture in a bone. The bone generally has a length of 10 cm or more, suitably 20 cm or more, more suitably 30 cm or more.

Generally, the bone is a tibia or femur.

The apparatus of the present invention is generally suitable for use with a patient such as a mammal, in particular a human although mention may be made of dogs, pigs, cows horses and camels.

Kit of Parts

According to a further aspect of the present invention there is provided a kit of parts comprising the apparatus as described herein, and instructions for use.

Typically, the kit includes more than one guide arm of differing lengths, in particular in order to cover the available range of intramedullary devices available. Generally, the guide arm forms part of a guide arm assembly, also including a second arm. Generally, the kit includes two to four guide arm assemblies of differing length.

Alternatively, the kit may include a single guide arm.

Suitably the kit includes a guide block. The guide block advantageously includes one or more radio opaque markings. Suitably the guide block includes one or more holes through which the pin, screw or nail to fix the intramedullary device to the bone is inserted.

The guide block is generally suitable for attachment to the guide arm and the kit may include means for attachment, for instance a screw, and typically a clamping plate to be positioned between the screw and the guide arm.

The kit may include an adjustable screw or piston to be housed within the guide block, or through a wall of the guide block. The adjustable screw or piston is suitable in use, for pushing against the surface of the second arm facing away from the guide arm in order to move the guide arm towards the aligned position.

Generally, the kit includes detachable affixment means to detachably fix the apparatus to an intramedullary device.

Generally the kit includes instructions for use.

System

According to a further embodiment, there is provided a system including the apparatus as disclosed herein for affixing an intramedullary device, and generally an analytical instrument used to monitor the alignment of the longitudinal profile of the guide arm relative to the longitudinal profile of the intramedullary device. The system also can include a suitably programmed computer for carrying out one or more steps of the methods. For example, the suitably programmed computer can carry out or assist in one or more of measuring the alignment of the longitudinal profile of the guide arm relative to the longitudinal profile of the intramedullary device; and displaying information relating to the alignment of the guide arm and the intramedullary device.

Typically, the system includes the kit of parts as described above.

Generally, the system includes an X-ray generator, generally an X-ray image intensifier. In such embodiments, the apparatus includes radio opaque markers, for instance in the form of lines or strips. Where the radio opaque markers comprise lines, the guide arm may be adjusted into the angle of the lines are coincident with the longitudinal profile of the intramedullary device.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Further aspects and embodiments of the invention are set forth in the following description. The present invention is further described by way of example only with reference to the accompanying Figures in which.

Figure 1:
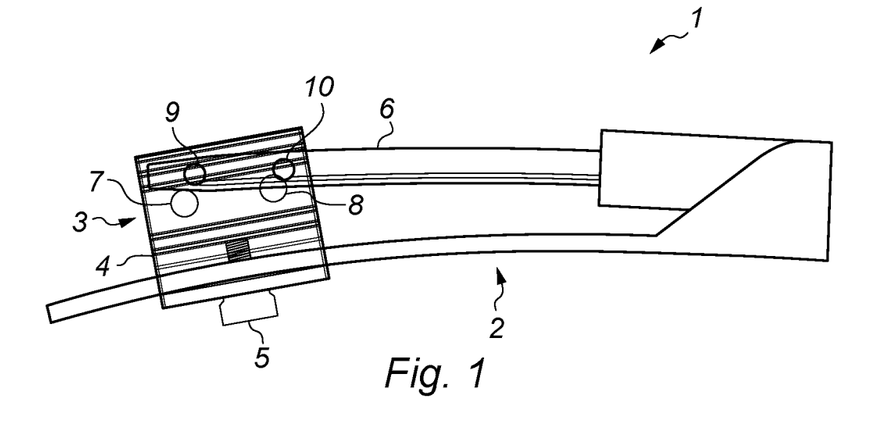
FIG. 1 shows an apparatus of the present invention wherein the guide arm is in the non-aligned position.

FIG. 1 shows a view of an apparatus of the present invention 1 attached to a slightly curved IM nail 6 including two holes 9, 10 towards the distal end of the IM nail 6 through which two pins may extend to secure the distal end of the IM nail. The apparatus 1 includes a guide arm 2, attached to a guide block 3 including radio opaque strips 4, and two holes 7, 8 through which pins to secure the IM nail may extend, typically following alignment. The guide block includes an adjustment screw 5, which moves the guide arm 6 towards the aligned position through straightening the guide arm 2. It can be observed from FIG. 1 that when the guide arm is in the non-aligned position, the radio opaque strips 4 are out of alignment with the longitudinal profile of the intramedullary device, and the holes 7, 8 in the guide block 3 are substantially out of alignment with the holes 9, 10 in the IM nail 6.

Figure 2:
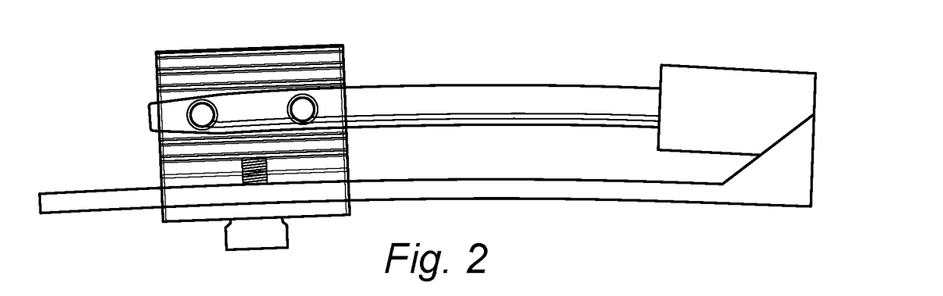
FIG. 2 shows an apparatus of the present invention wherein the guide arm is in the aligned position.

As shown in FIG. 2, as the guide arm 2 moves into alignment with the IM nail 6, resulting in the longitudinal profile of the guide arm 2 being substantially parallel to the longitudinal profile of the IM nail 6, the radio opaque strips 4 are also substantially parallel to the longitudinal profile of the IM nail 6, and the holes 7, 8 in the guide block 3 are substantially in alignment with the holes 9, 10 in the IM nail 6. Two holes can then be drilled in the bone surrounding the IM nail 6 at the location of the two holes 7, 8 in the guide block 3 in the aligned position. Pins (not shown) can then be inserted through the holes 7, 8 in the guide block 3, through the holes in the bone and through the holes 9, 10 in the IM nail 6, to secure the IM nail 6 to the bone.

Figure 3:
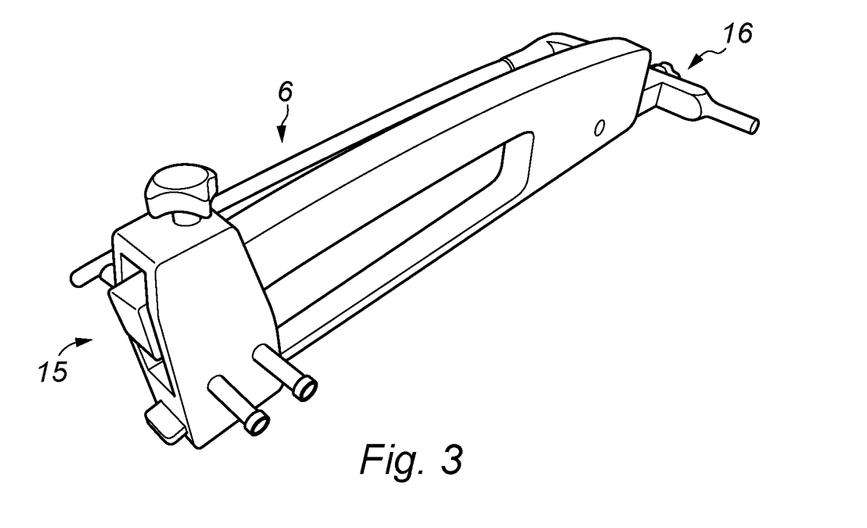
FIG. 3 shows an embodiment of an apparatus of the present invention.
Figure 4:
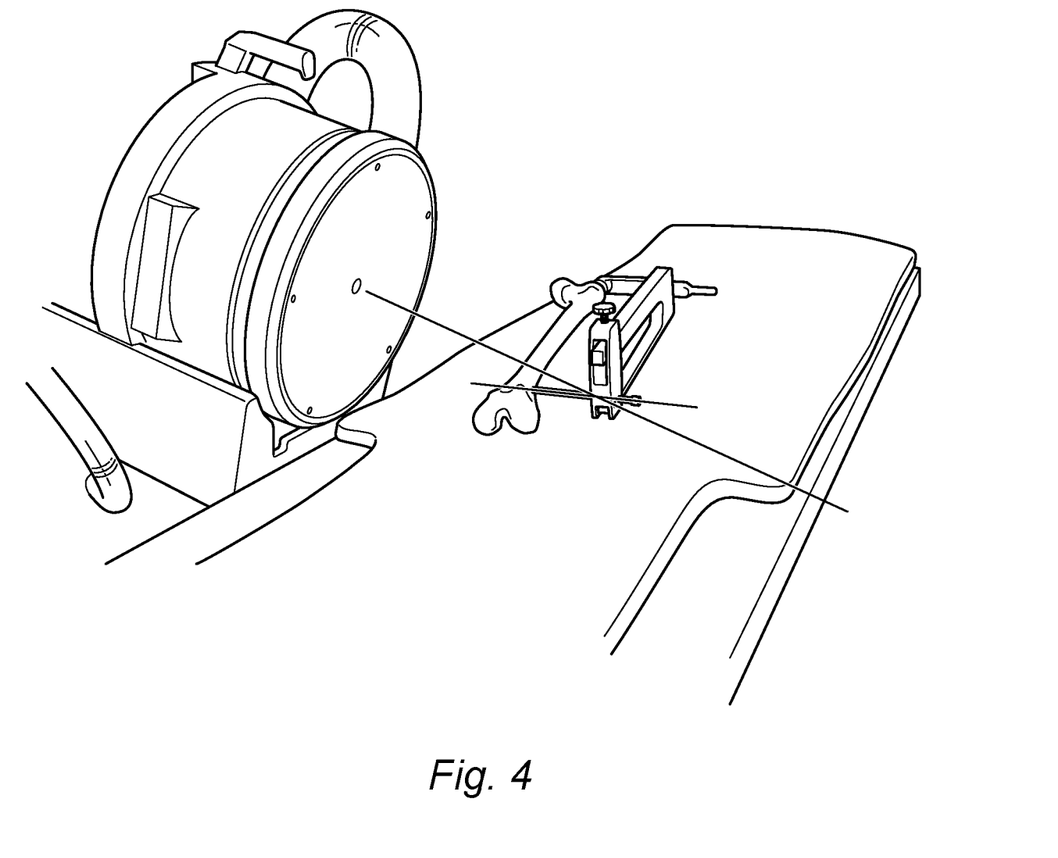
FIG. 4 shows the apparatus of FIG. 3 in a test situation, being used to position pins into an IM nail implanted within a bone, in use with an X-ray image intensifier.
Figure 5:
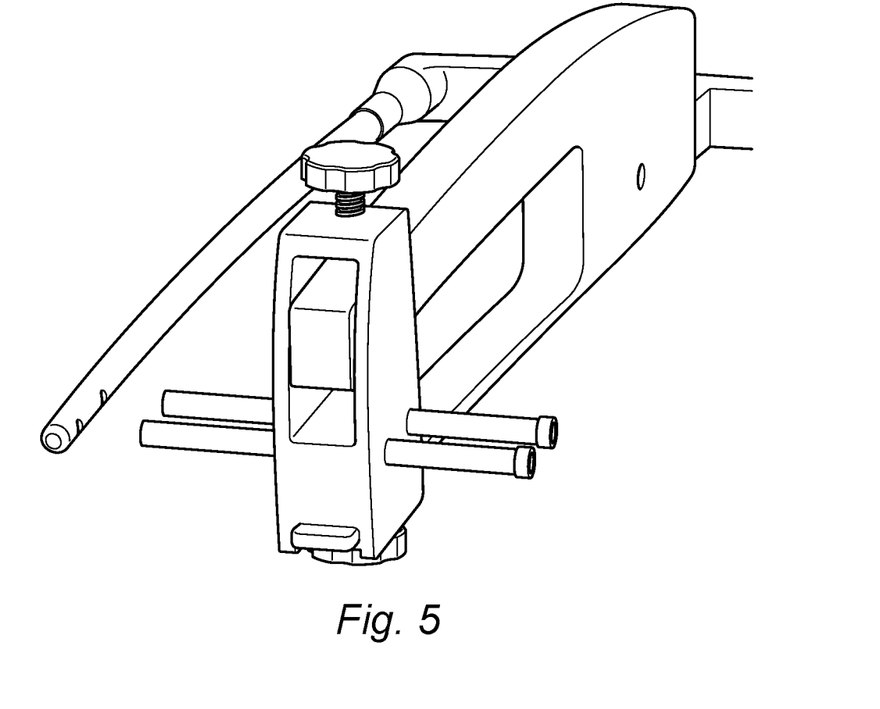
FIG. 5 shows the embodiment of the apparatus as shown in FIGS. 3 and 4 where the guide arm is in the aligned position.
Figure 6:
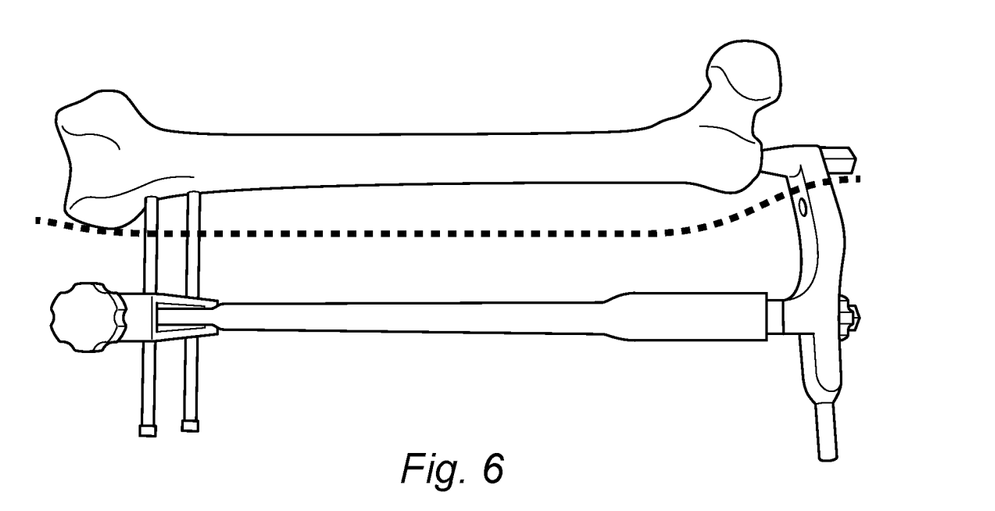
FIG. 6 shows the embodiment of the apparatus as shown in FIGS. 3 to 5 from above, with an arm fixing the proximal end of the jig to a bone.
Figure 7:
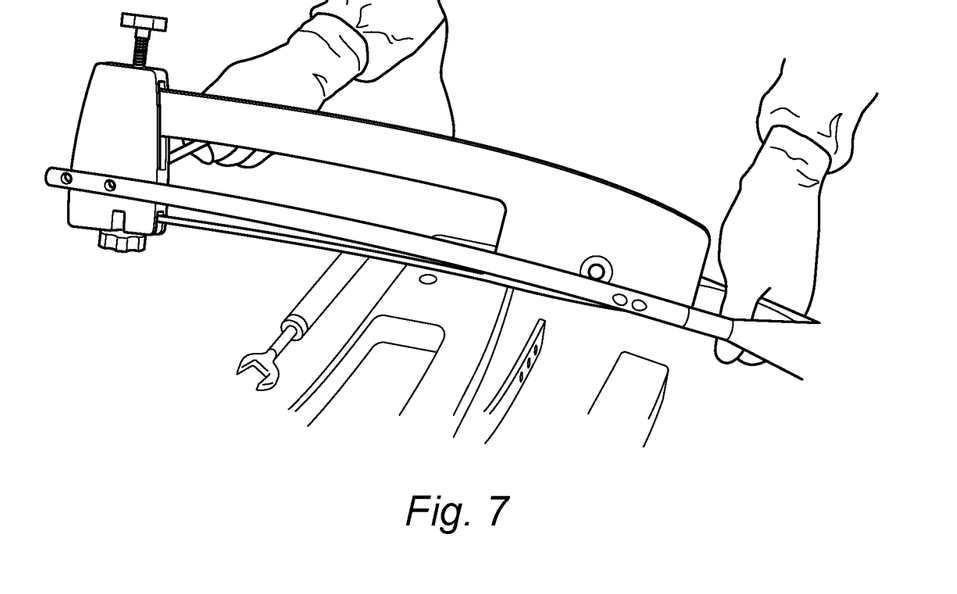
FIG. 7 shows a photograph of the apparatus as shown in FIGS. 3 to 6, attached to an IM nail, wherein the guide arm is in the non-aligned position.
Figure 8:
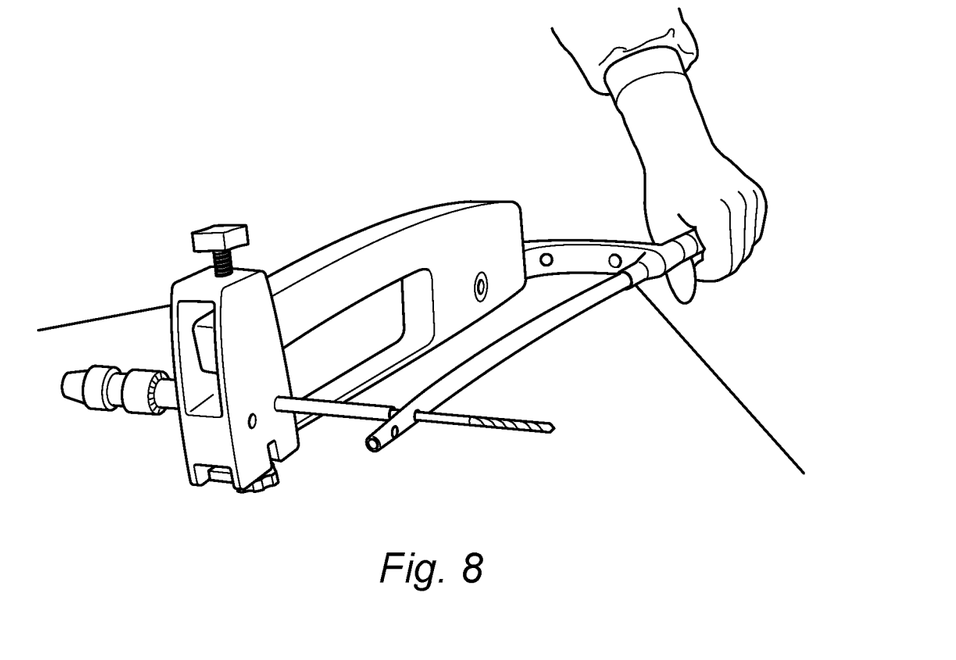
FIG. 8 shows a photograph of the assembly as shown in FIG. 7, wherein the guide arm is in the aligned position.

FIG. 3 shows a further embodiment of the apparatus of the present invention including a second arm 15. The jig as shown in FIG. 3 is attached to an IM nail 6 with a detachable affixment arm 16. FIG. 5 shows the assembly of FIG. 3 wherein the guide arm is in the aligned position. FIG. 6 illustrates that the apparatus of the present invention does not generally come into contact with the body of the patient during the method of affixing the intramedullary device. The detachable affixment arm extends away from the apparatus of the present invention. FIG. 7 shows the apparatus of the present invention in the initial non-aligned position. It may be noted that the guide arm is substantially out of alignment with the IM nail initially. The alignment adjustment mechanism moves the guide arm into the aligned position as shown in FIG. 8.

Figure 9:
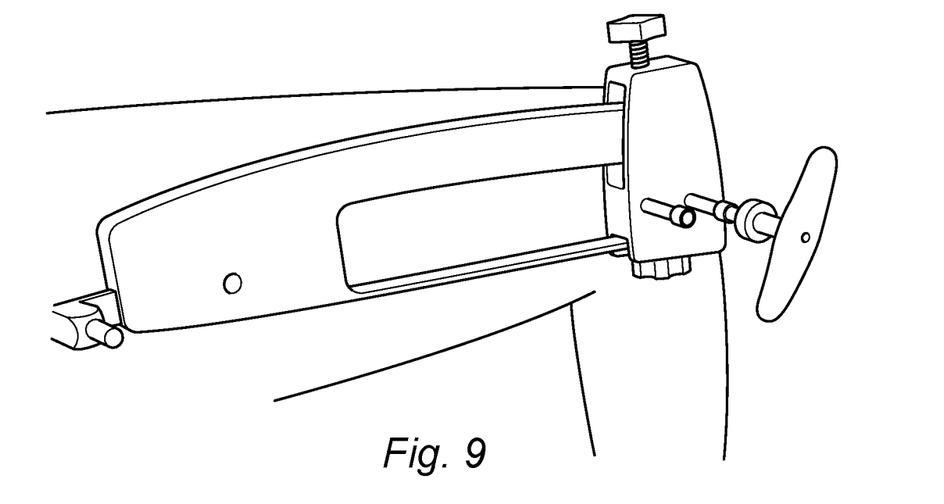
FIG. 9 shows a photograph of the apparatus as shown in FIGS. 3 to 8 in use and affixed to an intramedullary device which has been implanted into a patient.
Figure 10:
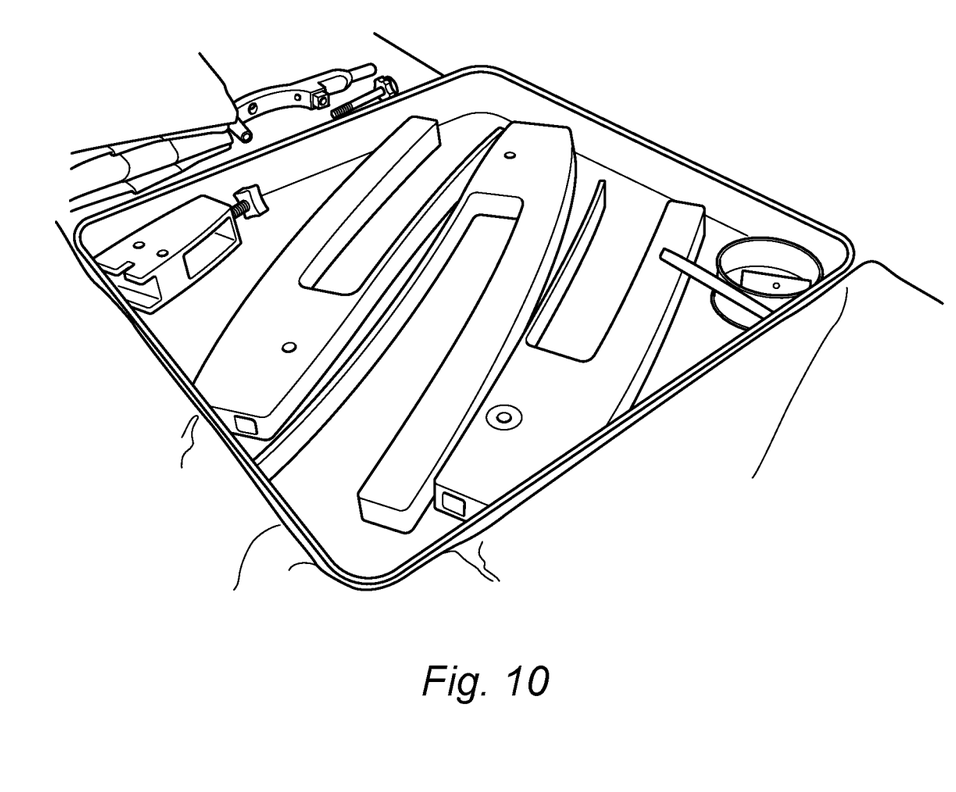
FIG. 10 shows a photograph of a kit including the apparatus of the present invention in dissembled form.
Figure 11:
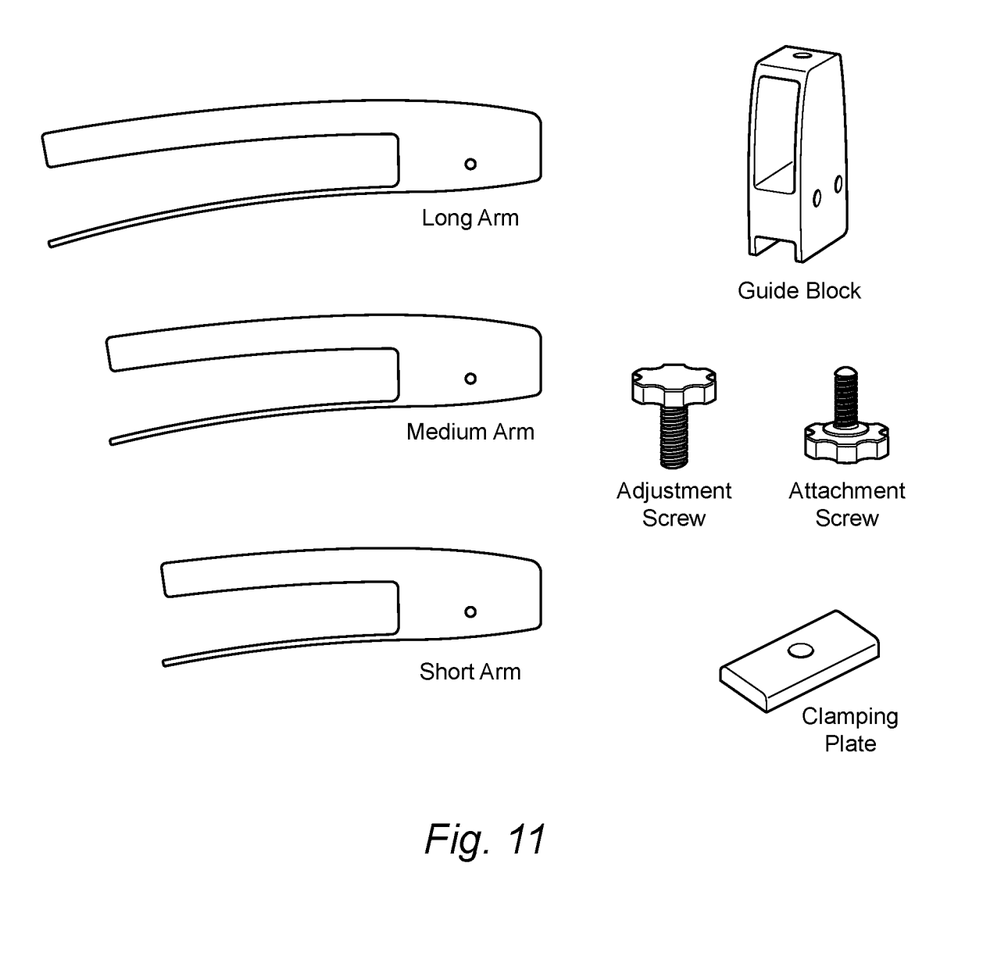
FIG. 11 provides a schematic representation of a kit including the apparatus of the present invention in dissembled form
Figure 12:
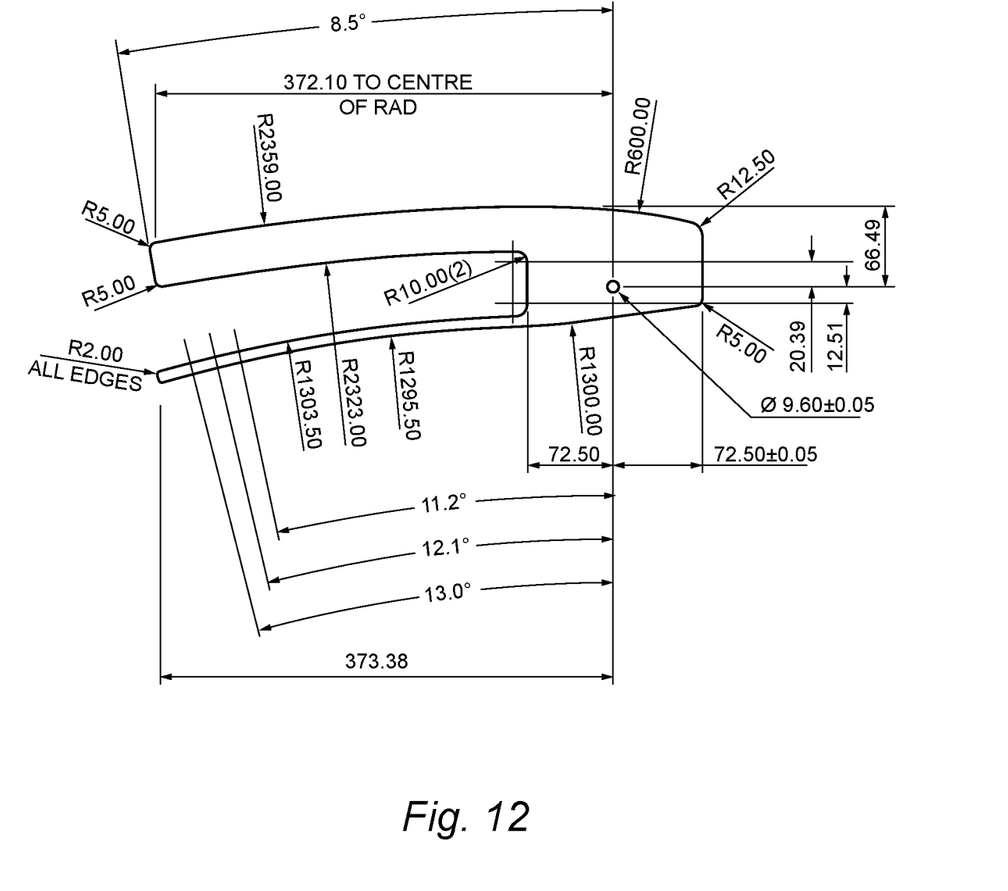
FIG. 12 shows an embodiment of the guide arm and the second arm of the present invention in the non-aligned position where all distances are provided in mm, and R is used to represent radius of curvature in mm.
Figure 13:
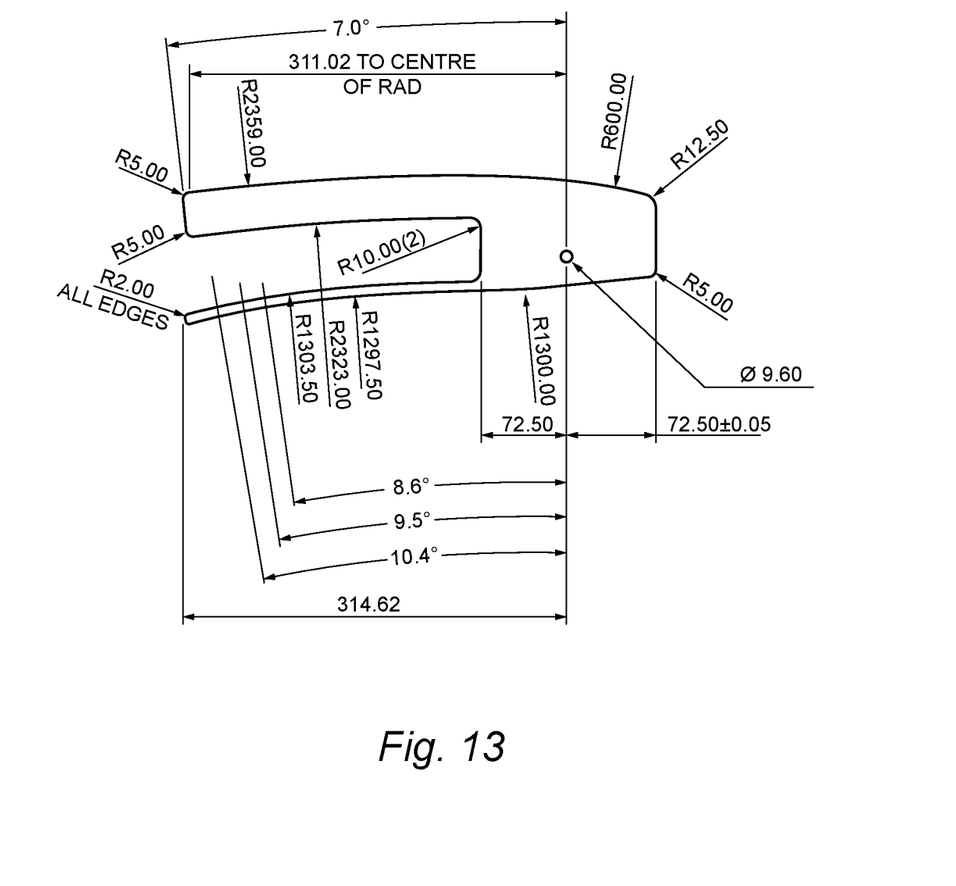
FIG. 13 shows an embodiment of the guide arm and the second arm of the present invention in the non-aligned position where all distances are provided in mm, and R is used to represent radius of curvature in mm.
Figure 14:
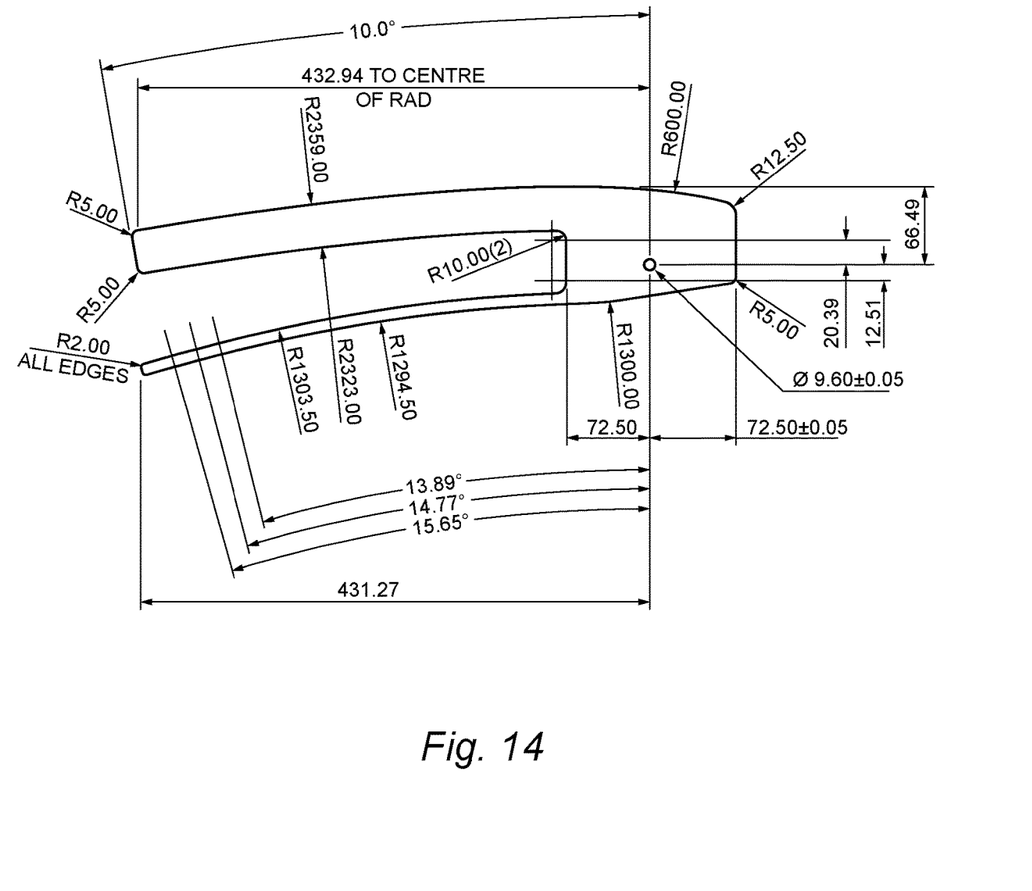
FIG. 14 shows an embodiment of the guide arm and the second arm of the present invention in the non-aligned position where all distances are provided in mm, and R is used to represent radius of curvature in mm.
Figure 15:
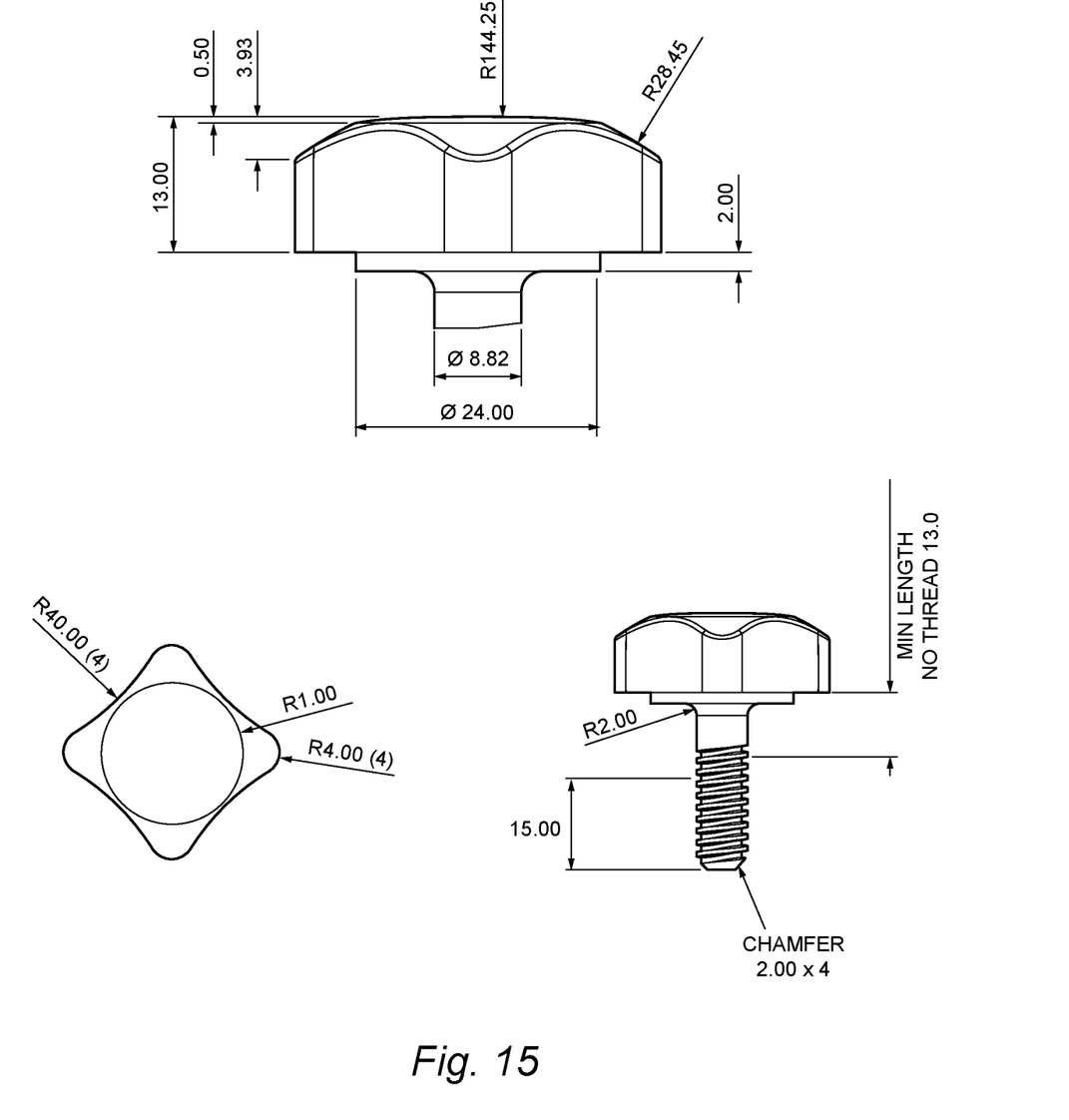
FIG. 15 shows three views of an adjustment screw suitable for use in the guide block, where all distances are provided in mm, and R is used to represent radius of curvature in mm.

As shown in FIG. 9, a protective sheet or layer (for instance a plastic protective sheet) may be placed between the apparatus of the present invention and the patient. The detachable affixment arm may extend through the protective sheet, but the apparatus itself does not contact the patient's body.

Various modifications and variations of the described aspects of the invention will be apparent to those skilled in the art

The invention claimed is:

1. An assembly comprising an apparatus for affixing an intramedullary device having a curved longitudinal profile, and the intramedullary device, the apparatus comprising:
a jig affixable to the intramedullary device at a proximal end, the jig comprising:
a guide arm having a proximal end and a distal end, the distal end being movable relative to the intramedullary device, the distal end movable between a non-aligned position in which the distal end is laterally spaced from a distal end of the intramedullary device, and an aligned position in which the distal end is aligned with the distal end of the intramedullary device, and
a second arm biased away from the guide arm in the aligned position;
a drill guide suitable for guiding an affixment towards the distal end of the intramedullary device,
an alignment adjuster to adjust an alignment of the guide arm relative to a longitudinal axis of the intramedullary device,
wherein in the non-aligned position, a longitudinal profile of the guide arm is curved between the proximal end and the distal end, wherein the curve of the longitudinal profile of the guide arm varies between the non-aligned position and the aligned position.

2. The assembly as claimed in claim 1, wherein a radius of curvature of the curved longitudinal profile of the guide arm is smaller than a radius of curvature of the curved longitudinal profile of the intramedullary device, and the radius of curvature of the longitudinal profile of the guide arm is greater in the aligned position than in the non-aligned position.

3. The assembly as claimed in claim 2, wherein in the non-aligned position, the longitudinal profile of the guide arm extends arcuately from the proximal end to the distal end away from the aligned position.

4. The assembly as claimed in claim 2, wherein in the non-aligned position, the radius of curvature of the guide arm is non-constant and varies at more than one point along its longitudinal profile, and the radius of curvature of the longitudinal profile of the guide arm is less than the radius of curvature of the longitudinal profile of the intramedullary device at each variation.

5. The assembly as claimed in claim 4, wherein the radius of curvature of the longitudinal profile of the guide arm varies at two or more points along its longitudinal profile.

6. The assembly as claimed in claim 4, wherein the radius of curvature alters within 50% of a length of the guide arm towards the proximal end.

7. The assembly as claimed in claim 4, wherein the radius of curvature alters within 30% of a length of the guide arm towards the proximal end and within 30% of the length of the guide arm towards the distal end.

8. The assembly as claimed in claim 2, wherein a maximum spacing between the guide arm and the second arm is in the non-aligned position.

9. The assembly as claimed in claim 1, wherein in the non-aligned position, a radius of curvature of the longitudinal profile of the guide arm is at least 10% less than a radius of curvature of the longitudinal profile of the intramedullary device.

10. The assembly as claimed in claim 1, wherein a radius of curvature of the curved longitudinal profile of the guide arm is greater than a radius of curvature of the curved longitudinal profile of the intramedullary device, and the radius of curvature of the longitudinal profile of the guide arm is smaller in the aligned position than the radius of curvature of the longitudinal profile of the guide arm in the non-aligned position.

11. The assembly as claimed in claim 10, wherein in the non-aligned position, the radius of curvature of the longitudinal profile of the guide arm is at least 10% greater than the radius of curvature of the longitudinal profile of the intramedullary device.

12. The assembly as claimed in claim 10, wherein in the non-aligned position, the radius of curvature of the guide arm is non-constant and varies at more than one point along its longitudinal profile, and the radius of curvature of the longitudinal profile of the guide arm is greater than the radius of curvature of the longitudinal profile of the intramedullary device at each variation.

13. The assembly as claimed in claim 10, wherein a minimum spacing between the guide arm and the second arm is in the non-aligned position.

14. The assembly claimed in claim 1, further comprising a radio translucent portion and at least one radio opaque marking at or towards the distal end.

15. The assembly as claimed in claim 1, wherein movement of the guide arm between the non-aligned and the aligned position occurs in a substantially lateral plane relative to the intramedullary device.

16. The assembly as claimed in claim 1, wherein the alignment adjuster is mounted around or through the second arm and is fixedly attached to the guide arm.

17. The assembly as claimed in claim 1, wherein the second arm is at least twice as rigid as the guide arm.

18. A kit of parts including the assembly as claimed in claim 1 and instructions for use.

19. A system including the assembly as claimed in claim 1, and an analytical instrument used to monitor the alignment of the longitudinal axis of the guide arm relative to the longitudinal axis of the intramedullary device and a suitably programmed computer.

* * * * *